(12) United States Patent
Yano et al.

(10) Patent No.: US 10,813,816 B2
(45) Date of Patent: Oct. 27, 2020

(54) PATIENT PLACEMENT TABLE MOVING METHOD USED ON ROBOTIC OPERATING TABLE

(71) Applicants: MEDICAROID CORPORATION, Kobe-shi, Hyogo (JP); SYSMEX CORPORATION, Kobe-shi, Hyogo (JP)

(72) Inventors: Yutaro Yano, Kobe (JP); Yukihiko Kitano, Kobe (JP); Yoshiyuki Tamura, Kobe (JP); Kenichi Nakagawa, Kobe (JP)

(73) Assignees: MEDICAROID CORPORATION, Kobe-shi (JP); SYSMEX CORPORATION, Kobe-shi (JP)

( * ) Notice: Subject to any disclaimer, the term of this patent is extended or adjusted under 35 U.S.C. 154(b) by 223 days.

(21) Appl. No.: 15/928,145

(22) Filed: Mar. 22, 2018

(65) Prior Publication Data

US 2018/0271732 A1 Sep. 27, 2018

(30) Foreign Application Priority Data

Mar. 23, 2017 (JP) ................................ 2017-057777

(51) Int. Cl.
*A61G 13/04* (2006.01)
*A61B 6/04* (2006.01)
(Continued)

(52) U.S. Cl.
CPC ............ *A61G 13/04* (2013.01); *A61B 5/0555* (2013.01); *A61B 6/0407* (2013.01);
(Continued)

(58) Field of Classification Search
CPC .............................. A61N 5/10; A61N 2005/10
See application file for complete search history.

(56) References Cited

U.S. PATENT DOCUMENTS

| 6,508,586 B2* | 1/2003 | Oota | ...................... A61B 6/032 |
| | | | 378/194 |
| 7,233,645 B2* | 6/2007 | Feda | ..................... G01N 23/223 |
| | | | 378/102 |

(Continued)

FOREIGN PATENT DOCUMENTS

| EP | 1028684 B1 | 3/2004 |
| JP | H05-093404 U | 12/1993 |

(Continued)

OTHER PUBLICATIONS

The Japanese Office Action dated Mar. 5, 2019 in a counterpart Japanese patent application.

(Continued)

*Primary Examiner* — Thomas R Artman
(74) *Attorney, Agent, or Firm* — Metrolex IP Law Group, PLLC

(57) ABSTRACT

A patient placement table moving method may be used with a robotic operating table including a patient placement table, a base buried in or fixed to a floor and an articulated robotic arm including joints and having first and second ends. The first end may be supported on the base to be rotatable about an axis extending in a vertical direction. The second end may support the table. The method may include: horizontally arranging the table by the robotic arm at an imaging position for imaging with a medical imaging apparatus; and translating the table from the imaging position to a surgical operation position by the robotic arm. The surgical operation position may be away from the imaging position by 200 mm or more in a second direction orthogonal to a first direction in a horizontal plane, and the first direction is parallel with a longitudinal direction of the table.

19 Claims, 8 Drawing Sheets

(51) Int. Cl.
*A61G 1/04* (2006.01)
*A61B 6/00* (2006.01)
*A61B 34/30* (2016.01)
*A61B 5/055* (2006.01)
*A61G 13/06* (2006.01)
*A61B 5/00* (2006.01)

(52) U.S. Cl.
CPC .............. *A61B 6/0487* (2020.08); *A61B 6/40* (2013.01); *A61B 34/30* (2016.02); *A61G 1/04* (2013.01); *A61G 13/06* (2013.01); *A61B 5/0036* (2018.08); *A61B 6/4441* (2013.01); *A61G 2203/14* (2013.01); *A61G 2203/16* (2013.01); *A61G 2210/50* (2013.01)

(56) References Cited

U.S. PATENT DOCUMENTS

| | | | |
|---|---|---|---|
| 7,623,623 B2* | 11/2009 | Raanes | A61N 5/1049 378/205 |
| 7,639,784 B2* | 12/2009 | Feda | G01N 23/223 378/106 |
| 7,669,261 B2 | 3/2010 | Früh et al. | |
| 7,860,550 B2 | 12/2010 | Saracen et al. | |
| 8,126,114 B2 | 2/2012 | Naylor et al. | |
| 8,160,205 B2 | 4/2012 | Saracen et al. | |
| 9,326,907 B2 | 5/2016 | Marle | |
| 9,950,194 B2* | 4/2018 | Bouchet | A61N 5/1049 |
| 10,028,714 B2* | 7/2018 | Dinse | A61B 6/548 |
| 2002/0039403 A1* | 4/2002 | Oota | A61B 6/032 378/196 |
| 2007/0217575 A1 | 9/2007 | Kaiser et al. | |
| 2009/0003523 A1* | 1/2009 | Raanes | A61N 5/1049 378/65 |
| 2011/0066278 A1 | 3/2011 | Pinault et al. | |
| 2015/0000038 A1 | 1/2015 | Obi | |
| 2015/0327818 A1* | 11/2015 | Buck | A61B 6/0457 5/608 |
| 2016/0067525 A1* | 3/2016 | Bouchet | A61N 5/1049 600/1 |
| 2018/0110486 A1* | 4/2018 | Suga | A61B 34/71 |
| 2018/0146932 A1* | 5/2018 | Suga | A61B 6/0457 |
| 2018/0177469 A1* | 6/2018 | Suga | A61B 6/0407 |
| 2018/0177470 A1* | 6/2018 | Suga | A61B 6/0407 |
| 2018/0242928 A1* | 8/2018 | Kochi | A61B 5/7225 |
| 2018/0242929 A1* | 8/2018 | Yano | A61B 6/548 |
| 2018/0243150 A1* | 8/2018 | Yano | A61G 13/04 |
| 2018/0243152 A1* | 8/2018 | Yano | A61G 13/04 |
| 2018/0271732 A1* | 9/2018 | Yano | A61G 13/04 |
| 2018/0280223 A1* | 10/2018 | Hiratsuka | A61B 90/50 |
| 2018/0289574 A1* | 10/2018 | Hiratsuka | A61N 5/10 |
| 2018/0289575 A1* | 10/2018 | Hiratsuka | A61B 5/0555 |

FOREIGN PATENT DOCUMENTS

| | | |
|---|---|---|
| JP | H06-048644 U | 7/1994 |
| JP | H08-126990 A | 5/1996 |
| JP | 2000-232969 A | 8/2000 |
| JP | 2000-342639 A | 12/2000 |
| JP | 2006-263894 A | 10/2006 |
| JP | 2007-236806 A | 9/2007 |
| JP | 2008-136797 A | 6/2008 |
| JP | 2012-005557 A | 1/2012 |
| JP | 2012-506748 A | 3/2012 |
| JP | 2014-100301 A | 6/2014 |
| JP | 2016-054860 A | 4/2016 |
| JP | 2016-165454 A | 9/2016 |

OTHER PUBLICATIONS

The Japanese Office Action dated Oct. 8, 2019 in a counterpart Japanese patent application.
Japanese Office Action dated Jul. 14, 2020 in a counterpart Japanese patent application.

* cited by examiner

PATIENT TRANSFER POSITION

ANESTHETIZATION POSITION

PATIENT PLACEMENT TABLE MOVING METHOD USED ON ROBOTIC OPERATING TABLE

CROSS REFERENCE TO RELATED APPLICATIONS

This application claims priority from prior Japanese Patent Application No. 2017-057777 filed with the Japan Patent Office on Mar. 23, 2017, the entire contents of which are incorporated herein by reference.

BACKGROUND

The disclosure relates to a patient placement table moving method used on a robotic operating table.

Japanese Patent Application Publication No. 2014-100301 discloses a hybrid operating room system in which a radiographic fluoroscopic imaging apparatus and an operating table are combined. In Japanese Patent Application Publication No. 2014-100301, the operating table includes a movable top plate on which a subject (patient) is placed and a base portion that supports the movable top plate. In the operating table, the movable top plate is configured to be movable by sliding parallel to a horizontal direction along the base portion fixed to a floor. Moreover, in the operation table, the base portion is configured to be extendable and contractible in the vertical direction to be capable of lifting and lowering the movable top plate in the vertical direction.

SUMMARY

In the conventional operating table as described in Japanese Patent Application Publication No. 2014-100301, the table (movable top plate) can be moved about 600 mm to 1000 mm in the longitudinal direction thereof. However, the table can be moved in the transverse direction thereof by such an amount that only fine adjustment can be performed (about 100 mm toward each of one side and the other side). In brain surgery, radiographic imaging or radiographic fluoroscopy needs to be performed alternately with treatment on the patient. Accordingly, there is a demand to perform a surgical operation near the imaging position to lessen the burden on the patient as much as possible.

Moreover, an arm for radiographic imaging in a floor-standing radiographic imaging apparatus has a small movement range and the main body of the radiographic imaging apparatus needs to be disposed near the operating table. Furthermore, in addition to the radiographic imaging apparatus, multiple monitors for observing radiographic projection images, a surgical microscope device, an anesthesia machine, a machine table, an infusion stand, a wagon for stents, an electrical surgical unit, and the like need to be disposed near the operation table. Accordingly, the operating table that can be moved in the transverse direction of the table by such an amount that only the fine adjustment can be performed has a problem that it is difficult to leave an enough space at a position where a surgeon (operator) stands on the head side of the patient and an enough space at positions where other medical staffs stand beside the operating table.

One or more embodiments may provide a patient placement table moving method that can leave spaces for a surgeon and other medical staffs at positions optimal for a surgical operation near an imaging position with higher freedom than in a conventional method of arranging a patient with an operating table for a hybrid operating room.

According to one or more embodiments, a patient placement table moving method may be for use with a robotic operating table including a patient placement table on which the patient is placed, a base that is buried in or fixed to a floor and an articulated robotic arm including a plurality of joints and having first and second ends. The first end may be supported on the base to be rotatable about an axis extending in a vertical direction, and the second end may support the table. The method may include: horizontally arranging the table by the robotic arm at an imaging position for imaging with a medical imaging apparatus; and translating the table from the imaging position to a surgical operation position by the robotic arm. The surgical operation position may be away from the imaging position by a distance of 200 mm or more in a second direction which is orthogonal to a first direction in a horizontal plane, and the first direction may be parallel with a longitudinal direction of the table.

According to one or more embodiments, a patient placement table moving method may be used on a robotic operating table including a patient placement table on which the patient is placed, a base that is buried in or fixed to a floor and an articulated robotic arm including a plurality of joints, and having first and second ends. The first end may be supported on the base to be rotatable about an axis extending in a vertical direction and the second end may supports the table. The method may include: horizontally arranging the table by the robotic arm at an imaging position for imaging with a medical imaging apparatus; translating the table from the imaging position to a certain position by the robotic arm; and translating the table from the certain position to a surgical operation position. The certain position may be away from the imaging position by a distance of 1000 mm or less in a first direction parallel with a longitudinal direction of the table, and the surgical operation position may be away from the certain position by a distance of 200 mm or more in a second direction orthogonal to the first direction in a horizontal plane.

According to one or more embodiments, a patient placement table moving method may be with use a robotic operating table including a patient placement table on which the patient is placed, a base that is buried in or fixed to a floor and an articulated robotic arm including a plurality of joints, and having first and second ends. The first end may be supported on the base to be rotatable about an axis extending in a vertical direction and the second end may support a portion of the table on a first end side in a longitudinal direction of the table. The method may include: horizontally arranging the table by the robotic arm at an imaging position for imaging with a medical imaging apparatus; and moving the table by the robotic arm from the imaging position to a surgical operation position by rotating the table in a horizontal plane within a range of 10 degrees or more and 45 degrees or less about a vertical axis, which is positioned on a second end side in the longitudinal direction of the table.

BRIEF DESCRIPTION OF DRAWINGS

FIG. 5A is a view illustrating an imaging position in propeller rotation imaging of the head of a patient, FIG. 5B is a view illustrating an imaging position in single-plane imaging of the head of a patient, FIG. 5C is a view illustrating an imaging position in biplane imaging of the head of a patient, and FIG. 5D is a view illustrating an imaging position in single-plane imaging of the right arm of a patient;

FIG. 6A is a view illustrating a surgical operation position in a case where a table is translated toward the right arm side of a patient, FIG. 6B is a view illustrating a surgical operation position in the case where the table is translated toward the right arm side of a patient and also toward the foot side of the patient, FIG. 6C is a view illustrating a surgical operation position in a case where the table is translated toward the foot side of a patient, FIG. 6D is a view illustrating a surgical operation position in a case where the table is rotated about the head side of a patient toward the left arm side of the patient by 15 degrees, and FIG. 6E is a view illustrating a surgical operation position in a case where the table is rotated about the head side of a patient toward the left arm side of the patient by 25 degrees;

DETAILED DESCRIPTION

One or more embodiments are explained below based on the drawings.

(Configuration of Robotic Operating Table)

A configuration of a robotic operating table 100 according to one or more embodiments is described with reference to FIGS. 1 to 11.

Figure 1:
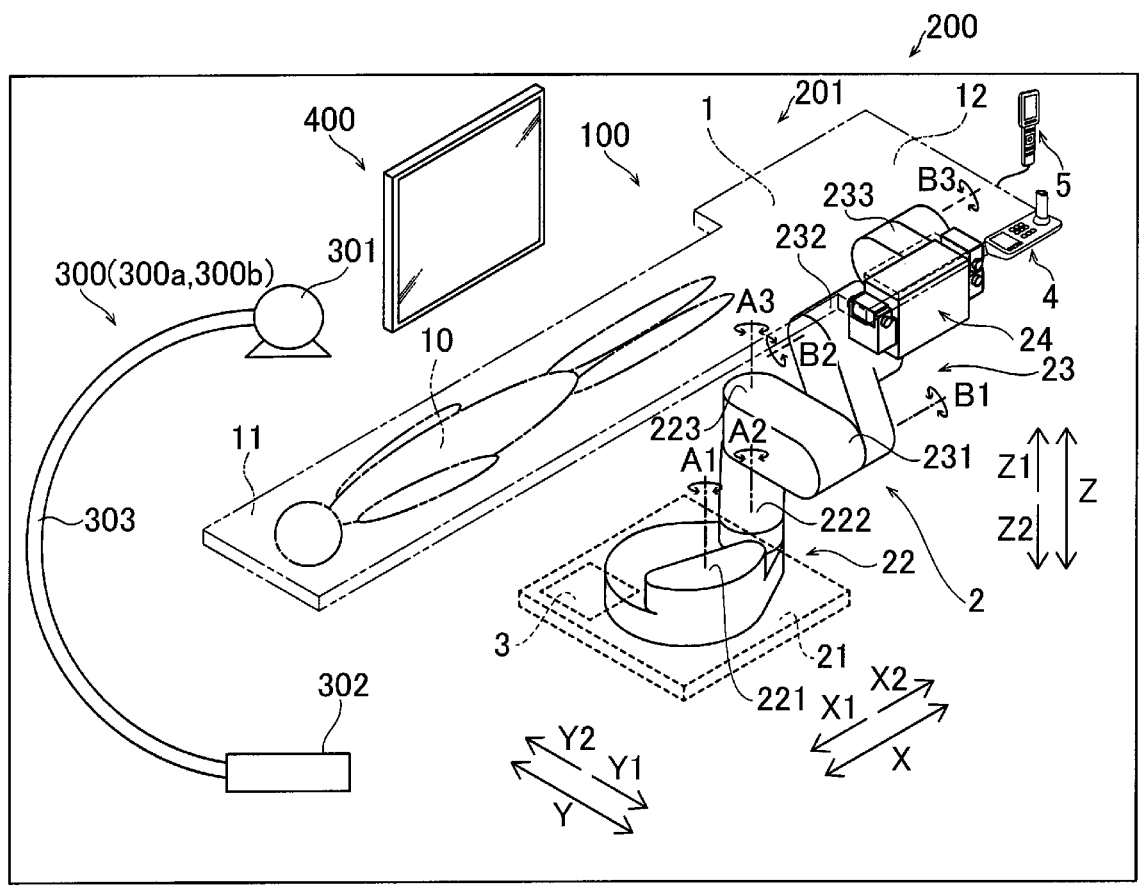
FIG. 1 is a schematic view illustrating an overview of an operating room including a robotic operating table according to one or more embodiments.

As illustrated in FIG. 1, the robotic operating table 100 is provided in an operating room 200. A radiographic imaging apparatus 300 that captures a radiographic projection image of a patient 10 is provided in the operating room 200. Specifically, an operating room system 201 including the robotic operating table 100 and the radiographic imaging apparatus 300 is provided in the operating room 200. The operating room 200 is a hybrid operating room. The radiographic imaging apparatus 300 includes a ceiling-suspended radiographic imaging apparatus 300a (see FIGS. 3 to 6) that is suspended from a ceiling of the operating room 200 and that can be linearly moved along a not-illustrated rail. Also, the radiographic imaging apparatus 300 includes a floor-standing radiographic imaging apparatus 300b (see FIGS. 3 to 6) that can be moved by an arm disposed on a floor of the operating room 200 to draw an arch-shaped trajectory. Moreover, a display 400 that displays information on a surgical operation is provided in the operating room 200. The display 400 is suspended by, for example, an arm (not illustrated) and is configured to be movable in the operating room 200. The display 400 is configured to display, for example, a radiographic projection image captured by the radiographic imaging apparatus 300. Note that the radiographic imaging apparatus 300 (300a, 300b) is an example of "medical imaging apparatus" in one or more recited embodiments.

The robotic operating table 100 is used as an operating table for performing a surgical operation in surgery, internal medicine, and the like. The robotic operating table 100 is configured to be capable of arranging a table 1 at a patient transfer position P1 (see FIG. 3) for transferring the patient 10. Moreover, the robotic operating table 100 is configured to be capable of arranging the patient 10 at an anesthetization position P2 (see FIG. 4), an imaging position P3 (see FIGS. 5A to 5D), a surgical operation position P4 (see FIGS. 6A to 6E), and the like by arranging the table 1 at the anesthetization position P2, the imaging position P3, the surgical operation position P4, and the like with the patient 10 placed on the table 1. Moreover, the robotic operating table 100 is configured to be capable of tilting the patient 10 by tilting the table 1 with the patient 10 placed on the table 1.

The robotic operating table 100 includes the table 1 on which the patient is placed, an articulated robotic arm 2 (hereafter, referred to as robotic arm 2), a robot controller 3, an operation device 4, and an operation device 5.

Figure 2:
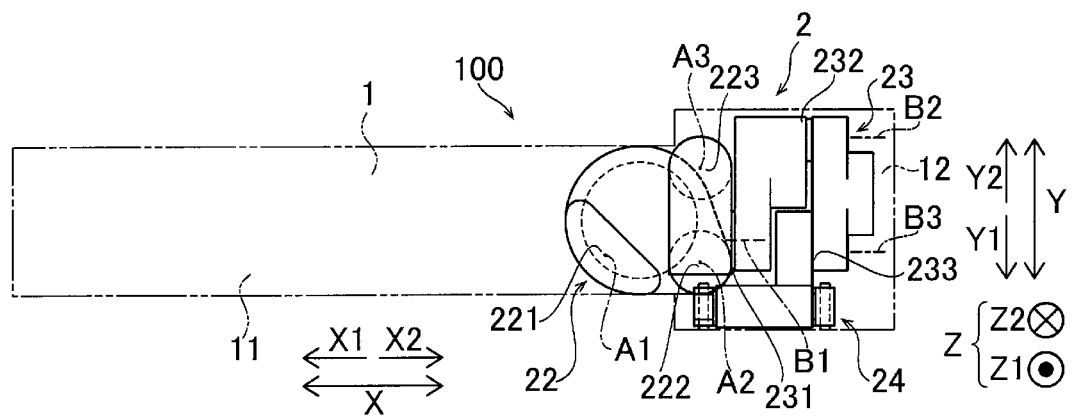
FIG. 2 is a plan view illustrating a robotic operating table according to one or more embodiments.

As illustrated in FIGS. 1 and 2, the table 1 is formed in a substantially-rectangular flat plate shape. Moreover, an upper surface of the table 1 is formed to be substantially flat. Note that the table 1 is rotatable about an axis extending in the vertical direction (Z direction). In this description, a horizontal direction parallel to the longitudinal direction of the table 1 is referred to as X direction, and a horizontal direction parallel to the transverse direction of the table 1 is referred to as Y direction. In other words, the X direction and the Y direction indicate directions based on the table 1. Note that the X direction and the Y direction are orthogonal to each other. Moreover, the X direction and the Y direction are examples of "first direction" and "second direction" in one or more recited embodiments, respectively.

The table 1 includes a radiolucent part 11 and a support unit 12 supporting the radiolucent part 11. The length of the table 1 in the X direction may be 2800 mm, the length of the radiolucent part 11 in the Y direction may be 500 mm, the length of the support unit 12 in the X direction may be 1000 mm, and the length of the support unit 12 in the Y direction may be 740 mm. The length of the table 1 in the X direction is preferably set to 2000 mm or more and 3000 mm or less, and the length of the table 1 in the Y direction is preferably set to 500 mm or more and 800 mm or less. The length of the radiolucent part 11 in the Y direction and the length of the support unit 12 in the Y direction are set to be the same or preferably set such that the length of the support unit 12 in the Y direction is longer than that of the radiolucent part 11.

The patient 10 is placed on the radiolucent part 11 of the table 1. The radiolucent part 11 is disposed on an X1 direction side of the table 1. The radiolucent part 11 is formed in a substantially-rectangular shape. The radiolucent part 11 is made of a material that tends to transmit X-ray. The radiolucent part 11 is made of, for example, a carbon material (graphite). The radiolucent part 11 is made of, for example, carbon fiber reinforced plastic (CFRP). The patient 10 can be thus imaged by using X-ray with the patient 10 placed on the radiolucent part 11.

The support unit 12 of the table 1 is connected to the robotic arm 2. The support unit 12 is disposed on an X2 direction side of the table 1. The support unit 12 is formed in a substantially-rectangular shape. The support unit 12 supports the radiolucent part 11. The support unit 12 is made of a material with a lower X-ray transmittance than the material of the radiolucent part 11. The support unit 12 is made of, for example, metal. The support unit 12 is made of, for example, an iron material or an aluminum material.

The table 1 is configured to be moved by the robotic arm 2. Specifically, the table 1 is configured to be movable in the X direction that is a horizontal direction, the Y direction that is a horizontal direction orthogonal to the X direction, and the Z direction that is a vertical direction orthogonal to the X direction and the Y direction. Moreover, the table 1 is configured to be capable of rotating (rolling) about an axis extending in the X direction. Furthermore, the table 1 is configured to be capable of rotating (pitching) about an axis extending in the Y direction. Moreover, the table 1 is configured to be capable of rotating (yawing) about an axis extending in the Z direction.

The robotic arm 2 is configured to move the table 1. One end of the robotic arm 2 is supported by a base 21 fixed to the floor and the other end of the robotic arm 2 supports the table 1. Specifically, the one end of the robotic arm 2 is configured to be supported by the base 21 to be rotatable about a base rotation axis (rotation axis A1) extending in the vertical direction (Z direction). The base 21 is a base portion buried in and fixed to the floor. The base 21 is provided substantially at a center of a movement range of the table 1 in a plan view (as viewed in the Z direction). Moreover, the other end of the robotic arm 2 is configured to support a portion of the table 1 that is adjacent to one end of the table 1 in the longitudinal direction (X direction) thereof. Specifically, the other end of the robotic arm 2 is configured to support the support unit 12 disposed adjacent to the one end of the table 1 in the longitudinal direction of the table 1. The robotic arm 2 can be thereby disposed away from a periphery of the radiolucent part 11 as much as possible, and a space large enough to dispose the radiographic imaging apparatus 300 can be thus left around the radiolucent part 11.

The robotic arm 2 is configured to be capable of being disposed in such a posture that substantially the entire robotic arm 2 is hidden below (on a Z2 direction side of) the table 1 in the plan view (as viewed in the Z1 direction). Moreover, the robotic arm 2 is configured to be capable of taking such a posture that the length thereof in the X direction parallel to the longitudinal direction of the table 1 is half or less the length of the table 1 in the longitudinal direction. A space whose length is half or more of the length of the table 1 in the longitudinal direction can be thereby left below the table 1 on the opposite side to the one end of the table 1 at which the table 1 is supported by the robotic arm 2, and a space large enough to dispose the radiographic imaging apparatus 300 can be thus left around the table 1 on which the patient is placed. From the view point of the strength of the robotic arm 2, the length of the robotic arm 2 in the X direction in the aforementioned posture is preferably quarter or more of the length of the table 1 in the longitudinal direction.

The robotic arm 2 includes a horizontal articulated assembly 22, a vertical articulated assembly 23, and a pitch mechanism 24. The horizontal articulated assembly 22 includes horizontal joints 221, 222, and 223. The vertical articulated assembly 23 includes vertical joints 231, 232, and 233. In one or more embodiments, the table 1 can be easily moved to a desired position in the horizontal direction by the horizontal articulated assembly 22 including the multiple horizontal joints 221, 222, and 223. Moreover, the table 1 can be easily moved to a desired position in the up-down direction by the vertical articulated assembly 23 including the multiple vertical joints 231, 232, and 233. Note that the horizontal joints 221 to 223 and the vertical joints 231 to 233 are examples of "joints" in one or more recited embodiments.

The robotic arm 2 is configured to move the table 1 with seven degrees of freedom. The range and freedom of the movement of the table 1 on which the patient 10 is placed can be thereby increased. Specifically, the horizontal articulated assembly 22 provides the robotic arm 2 three degrees of freedom of: rotating about the rotation axis A1 extending in the vertical direction; rotating about a rotation axis A2 extending in the vertical direction; and rotating about a rotation axis A3 extending in the vertical direction. Moreover, the vertical articulated assembly 23 provides the robotic arm 2 three degrees of freedom of: rotating about a rotation axis B1 extending in the horizontal direction, rotating about a rotation axis B2 extending in the horizontal direction; and rotating about a rotation axis B3 extending in the horizontal direction. Furthermore, the pitch mechanism 24 provides the robotic arm 2 one degree of freedom of causing the table 1 to pitch about a rotation axis extending in the transverse direction (Y direction) of the table 1.

Moreover, the robotic arm 2 is configured to cause the table 1 to yaw about an axis extending in the vertical direction (Z direction) by using at least one of the horizontal joints 221, 222, and 223. Furthermore, the robotic arm 2 is configured to cause the table 1 to roll about an axis extending in the longitudinal direction (X direction) by using at least one of the vertical joints 231, 232, and 233. Moreover, the robotic arm 2 is configured to cause the table 1 to pitch about an axis extending in the transverse direction (Y direction) by using the pitch mechanism 24. The robotic arm 2 is configured to cause the table 1 to roll, pitch, and yaw about the imaging position P3 (P3a) to be described later.

As illustrated in FIGS. 3 to 6E, the robotic arm 2 is configured to be capable of arranging the table 1 at the patient transfer position P1 (see FIG. 3), the anesthetization position P2 (see FIG. 4), the imaging position P3 (see FIGS. 5A to 5D), and the surgical operation position P4 (see FIGS. 6A to 6E). As described later, in the robotic operating table 100, the anesthetization position P2, the imaging position P3, and the surgical operation position P4 are registered in advance as preset positions, and the patient transfer position P1 is the same as the anesthetization position P2. Note that FIGS. 3 to 6E illustrate the patient transfer position P1, the anesthetization position P2, the imaging position P3, and the surgical operation position P4 in brain surgery.

Figure 3:
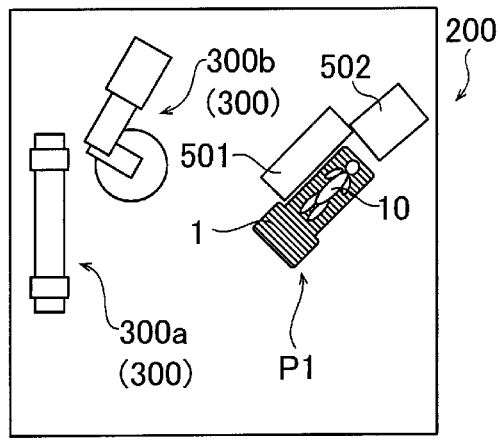
FIG. 3 is a view illustrating a patient transfer position of a robotic operating table according to one or more embodiments.

As illustrated in FIG. 3, the patient transfer position P1 is a position for transferring the patient 10 between the table 1 and a stretcher 501 for carrying the patient 10. Specifically, the patient transfer position P1 is a position for transferring the patient 10 from the stretcher 501 to the table 1 and a position for transferring the patient 10 from the table 1 to the stretcher 501. A position of the table 1 at which the stretcher 501 can be easily disposed beside the table 1 is registered as the patient transfer position P1. At the patient transfer position P1, the table 1 is disposed such that one side of the table 1 in the longitudinal direction thereof on the head side of the patient 10 faces opposite to the side where the radiographic imaging apparatus 300 is disposed. Also, at the patient transfer position P1, the table 1 is disposed such that the other side of the table 1 in the longitudinal direction thereof on the foot side of the patient 10 faces the side where the radiographic imaging apparatus 300 is disposed. When the patient 10 is placed on the table 1 at the patient transfer position P1, the ceiling-suspended radiographic imaging apparatus 300a, the floor-standing radiographic imaging apparatus 300b, the stretcher 501, an anesthesia machine 502, and the like are disposed around the table 1.

Figure 4:
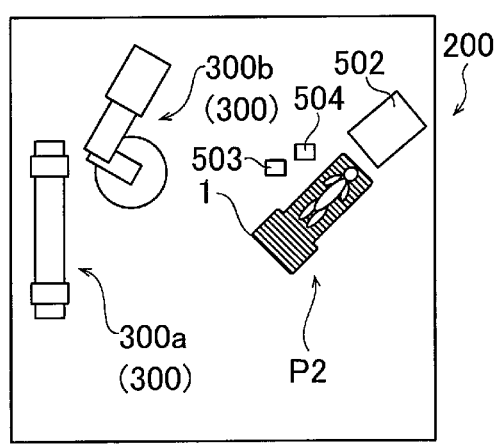
FIG. 4 is a view illustrating an anesthetization position of a robotic operating table according to one or more embodiments.

As illustrated in FIG. 4, the anesthetization position P2 is a position for performing anesthetization. A position of the table 1 at which the head of the patient 10 is close to the anesthesia machine 502 is registered as the anesthetization position P2. The anesthesia machine 502 is disposed opposite to the side where the radiographic imaging apparatus 300 is disposed in the operating room 200. Specifically, the anesthesia machine 502 is disposed opposite to the side of performing the surgical operation requiring cleanness. At the anesthetization position P2, the table 1 is disposed such that the one side of the table 1 in the longitudinal direction thereof on the head side of the patient 10 faces opposite to the side where the radiographic imaging apparatus 300 is disposed. Also, at the anesthetization position P2, the table 1 is disposed such that the other side of the table 1 in the longitudinal direction thereof on the foot side of the patient 10 faces the side where the radiographic imaging apparatus 300 is disposed. Note that, although the patient transfer position P1 and the anesthetization position P2 are the same position in one or more embodiments, the patient transfer position P1 and the anesthetization position P2 are not limited to this and may be positions different from each other. When the anesthetization is performed at the anesthetization position P2, the ceiling-suspended radiographic imaging apparatus 300a, the floor-standing radiographic imaging apparatus 300b, the anesthesia machine 502, an infusion device 503, a syringe pump 504, and the like are disposed around the table 1.

As illustrated in FIGS. 5A to 5D, the imaging position P3 is a position for imaging the patient 10 with the radiographic imaging apparatus 300. The imaging position P3 is, for example, a position P3a (see FIGS. 5A to 5C) for imaging the head of the patient 10 and a position P3b (see FIG. 5D) for imaging the right arm of the patient 10. Note that the imaging position P3 is not limited to this and may be a position for imaging the other portions of the patient 10. For example, the imaging position P3 may be a position for imaging the torso of the patient 10 or a position for imaging the left arm, the left leg, or the right leg of the patient 10. The position P3a for imaging the head of the patient 10 is registered as the imaging position P3.

Figure 5A:
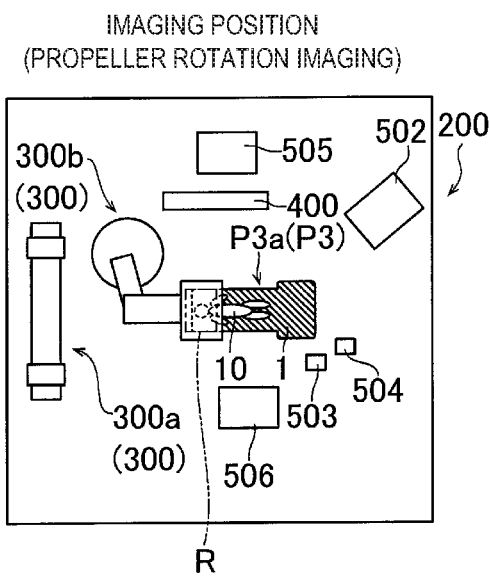
FIGS. 5A to 5D are views illustrating imaging positions of a robotic operating table according to one or more embodiments.
Figure 5B:
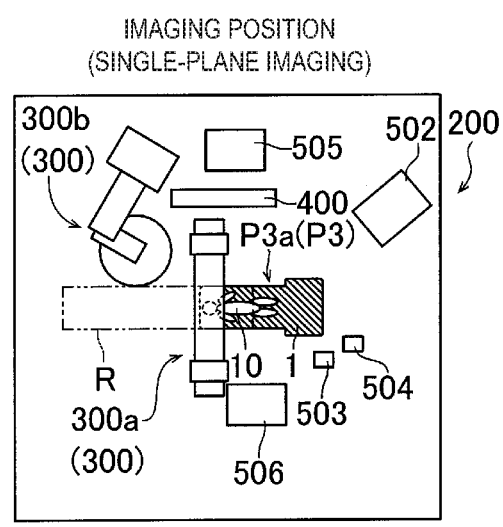
Figure 5C:
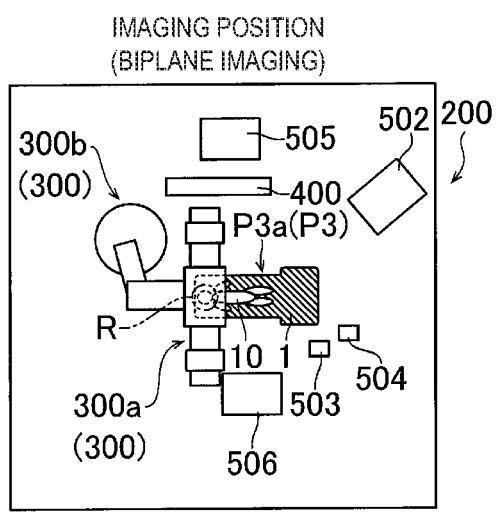
Figure 5D:
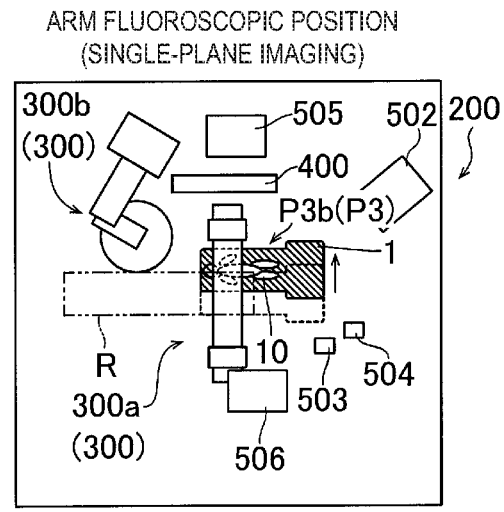

As illustrated in FIGS. 5A to 5C, the imaging position P3a is a position for performing propeller rotation imaging of the head of the patient 10 with the floor-standing radiographic imaging apparatus 300b, single-plane imaging of the head of the patient 10 with the ceiling-suspended radiographic imaging apparatus 300a, and biplane imaging of the head of the patient 10 with the ceiling-suspended radiographic imaging apparatus 300a and the floor-standing radiographic imaging apparatus 300b. Moreover, as illustrated in FIG. 5D, the position P3b is an arm fluoroscopic position for performing single-plane imaging of the right arm of the patient 10 with the ceiling-suspended radiographic imaging apparatus 300a. Furthermore, the arm fluoroscopic position P3b may be a position where the table 1 is translated from the imaging position P3a by 400 mm in a direction (Y2 direction) toward one side of the Y direction (see FIG. 1) which is the direction toward the left side of the patient 10. Note that, in FIG. 5D, the table 1 at the imaging position P3a is illustrated by broken lines to facilitate the understanding.

In FIG. 5A to 5D, an imaging region R of the radiographic imaging apparatus 300 (300a, 300b) is illustrated by two-dot chain lines. As illustrated in FIGS. 5A to 5C, the imaging position P3a is such a position that the head of the patient 10 is disposed in the imaging region R. Moreover, as illustrated in FIG. 5D, the arm fluoroscopic position P3b is such a position that the right arm of the patient 10 is disposed in the imaging region R. In other words, the imaging position P3 is such a position that the imaged portion of the patient 10 is disposed in the imaging region R. Moreover, at the imaging position P3a and the arm fluoroscopic position P3b, the table 1 is disposed such that the one side of the table 1 in the longitudinal direction thereof on the head side of the patient 10 faces the side where the radiographic imaging apparatus 300 is disposed and the other side of the table 1 in the longitudinal direction thereof on the foot side of the patient 10 faces opposite to the side where the radiographic imaging apparatus 300 is disposed. When the imaging is performed at the imaging position P3a and the arm fluoroscopic position P3b, the ceiling-suspended radiographic imaging apparatus 300a, the floor-standing radiographic imaging apparatus 300b, the display 400, the anesthesia machine 502, the infusion device 503, the syringe pump 504, a surgical microscope device 505, a wagon 506 for stents, and the like are disposed around the table 1.

As illustrated in FIGS. 6A to 6E, P4a to P4e are candidate positions of micro surgery positions at which micro surgery being a surgical operation using the surgical microscope device 505 is performed, The candidate positions P4a to P4e are positions where the table 1 is disposed such that spaces in which medical staffs (surgeon M1, other medical staffs M2, and the like) involved in the surgical operation can stand are provided around the table 1 and the surgeon M1 can easily perform the surgical operation (in the case of brain surgery, cranium opening). One of these candidate positions can be selected and registered as the surgical operation position P4.

Figure 6A:
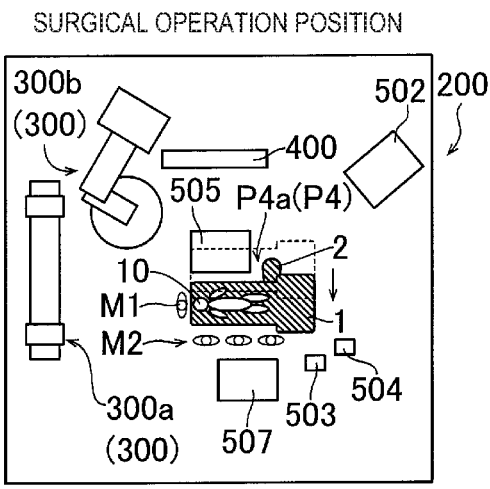
FIGS. 6A to 6E are views illustrating surgical operation positions of a robotic operating table according to one or more embodiments.
Figure 6B:
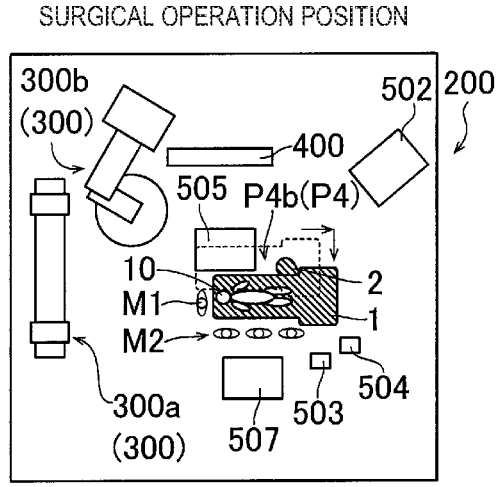
Figure 6C:
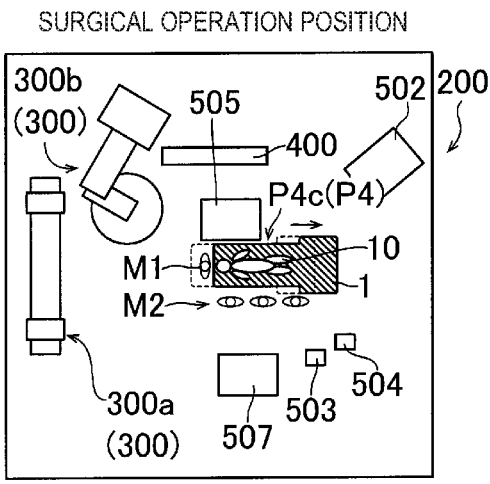
Figure 6D:
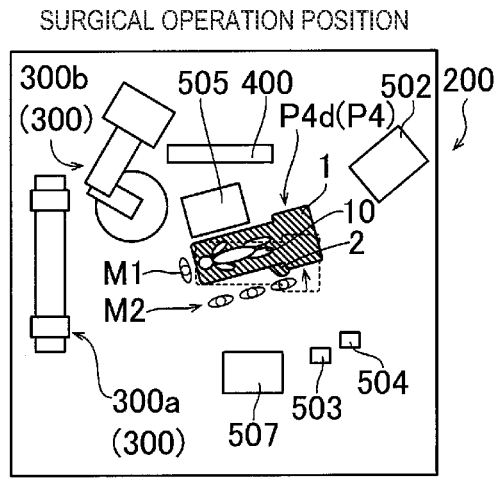
Figure 6E:
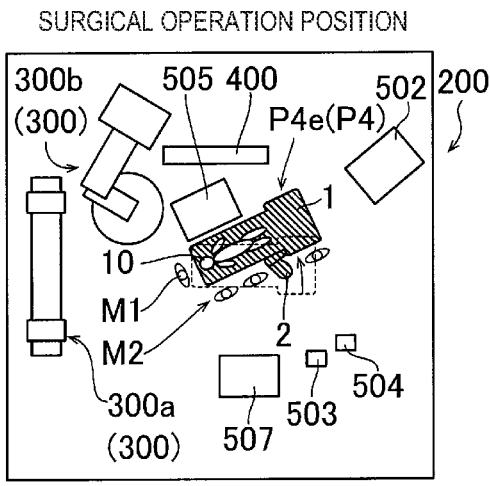
Figure 7:
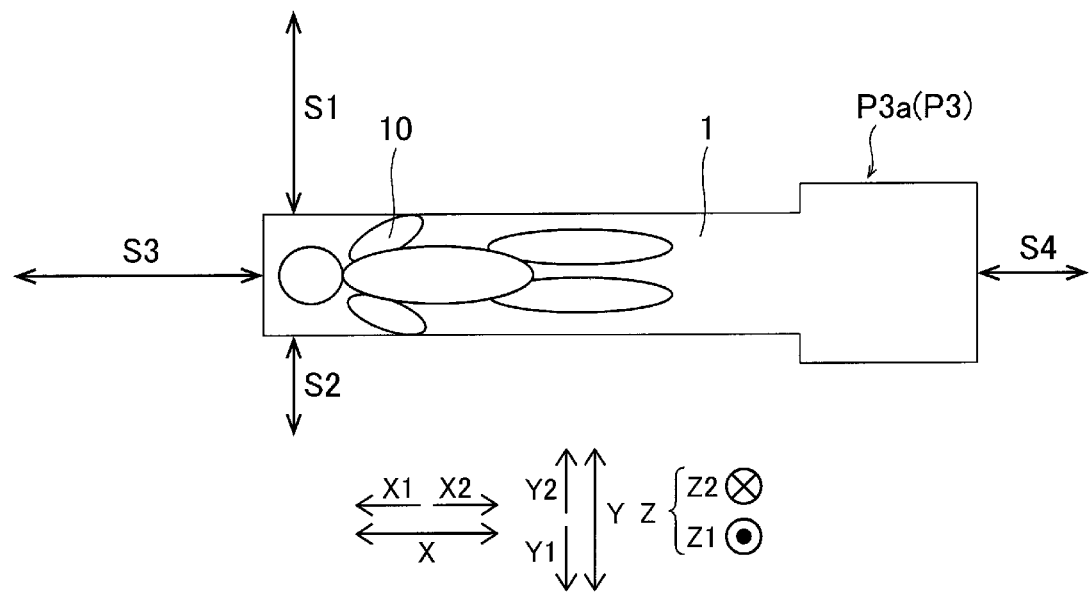
FIG. 7 is a view illustrating a translation movement range of a robotic operating table according to one or more embodiments.

In one or more embodiments, as illustrated in FIG. 7, the robotic arm 2 is configured to be capable of translating the table 1, from the state where the table 1 is horizontally arranged at the imaging position P3a being a reference position, in the X direction parallel to the longitudinal direction of the table 1. Moreover, the robotic arm 2 is configured to arrange the table 1 at the surgical operation position P4 (see FIGS. 6A to 6E) translated, from the imaging position P3a or from a position translated from the imaging position P3a in the X direction, by 200 mm or more in the Y direction orthogonal to the X direction in the horizontal plane. The surgical operation can be thus performed with the table 1 arranged at the surgical operation position P4 translated, from the imaging position P3a or from the position translated from the imaging position P3a in the X direction, within a relatively large movement range of 200 mm or more in the Y direction orthogonal to the X direction in the horizontal plane. Freedom in the adjustment of the surgical operation position P4 can be thereby increased. As a result, at the surgical operation position P4, it is possible to leave a space large enough for the surgeon M1 to stand on the head side of the patient 10 and leave a space large enough for the other medical staffs M2 to stand beside the operating table (table 1). The spaces for the surgeon M1 and the other medical staffs M2 can be left at positions optimal for the surgical operation. Moreover, freedom in the design of the hybrid operating room can be improved from that of the conventional operating table for the hybrid operating room. Furthermore, the table 1 in the conventional operating table for the hybrid operating room has a small movement range, and the conventional operation table is thus difficult to use for a general surgical operation (surgical operation using no radiographic imaging apparatus). However, the robotic operating table of one or more embodiments can be used for such a general surgical operation. Accordingly, when general operating rooms provided with no radiographic imaging apparatus are all used for surgical operations and only the hybrid operating room is vacant, the general surgical operation can be performed in the hybrid operating room.

Moreover, in one or more embodiments, the robotic arm 2 is configured to be capable of translating the table 1, from the imaging position P3a or from the position translated from the imaging position P3a in the X direction, within a total range of 1200 mm or less in the direction (Y2 direction) toward the one side of the Y direction and in a direction (Y1 direction) toward the other side of the Y direction. The table 1 can be thus translated in a wide range in the Y direction, and a more-appropriate position can be thereby set as the surgical operation position P4. Specifically, the robotic arm 2 is configured to be capable of translating the table 1, from the imaging position P3a or from the position translated from the imaging position P3a in the X direction, within a range S1 which is 800 mm or less in the Y2 direction which is the direction toward the left side of the patient 10. Moreover, the robotic arm 2 is configured to be capable of translating the table 1, from the imaging position P3a or from the position translated from the imaging position P3a in the X direction, within a range S2 which is 400 mm or less in the Y1 direction which is the direction toward the right side of the patient 10. In other words, the robotic arm 2 is configured such that the Y direction translatable range of the table 1, from the imaging position P3a or from the position translated from the imaging position P3a in the X direction, in the direction (Y2 direction) toward the one side of the Y direction is different from that in the direction (Y1 direction) toward the other side of the Y direction.

Moreover, in one or more embodiments, the robotic arm 2 is configured to be capable of translating the table 1, from the state where the table 1 is horizontally arranged at the imaging position P3a, within a range of 1500 mm or less in total in directions (X1 direction and X2 direction) toward one side and the other side of the X direction. Note that the robotic arm 2 is preferably configured to be capable of translating the table 1, from the state where the table 1 is horizontally arranged at the imaging position P3a, in the directions toward the one side and the other side of the X direction within a total range of 1000 mm or more and 2000 mm or less, preferably 1100 mm or more and 1600 mm or less. The robotic arm 2 can thereby translate the table 1 in the X direction within a range regarded as necessary in the operating room while achieving size reduction. Moreover, the robotic arm 2 is configured to be capable of translating the table 1 from the imaging position P3a within a range S3 which is 1000 mm or less in the X1 direction which is the direction toward the head of the patient 10. Furthermore, the robotic arm 2 is configured to be capable of translating the table 1 from the imaging position P3a within a range S4 which is 500 mm or less in the X2 direction which is the direction toward the foot side of the patient 10. In other words, the robotic arm 2 is configured such that the X-direction translatable range of the table 1, from the state where the table 1 is horizontally arranged at the imaging position P3a, in the direction (X1 direction) toward the one side of the X direction is different from that in the direction (X2 direction) toward the other side of the X direction.

Moreover, in one or more embodiments, the surgical operation position P4 is a position where the table 1 is translated, from the imaging position P3a, by 0 mm or more and 500 mm or less in the X direction and by 200 mm or more and 800 mm or less in the Y direction. The surgical operation position P4 is preferably a position where the table 1 is translated from the imaging position P3a by 0 mm or more and 500 mm or less in the X direction and by 250 mm or more and 600 mm or less in the Y direction. The surgical operation position P4 is more preferably a position where the table 1 is translated from the imaging position P3a by 0 mm or more and 300 mm or less in the X direction and by 300 mm or more and 500 mm or less in the Y direction. The surgical operation position P4 can be thereby set as a position that is close to the imaging position P3a and that can leave the spaces around the table 1. As a result, it is possible to reduce burden on the patient 10 due to movement between the imaging position P3a and the surgical operation position P4. In addition, at the surgical operation position P4, it is possible to provide a space where the surgeon M1 stands on the head side of the patient 10 and a space where the other medical staffs M2 stand beside the operating table (table 1).

Figure 8:
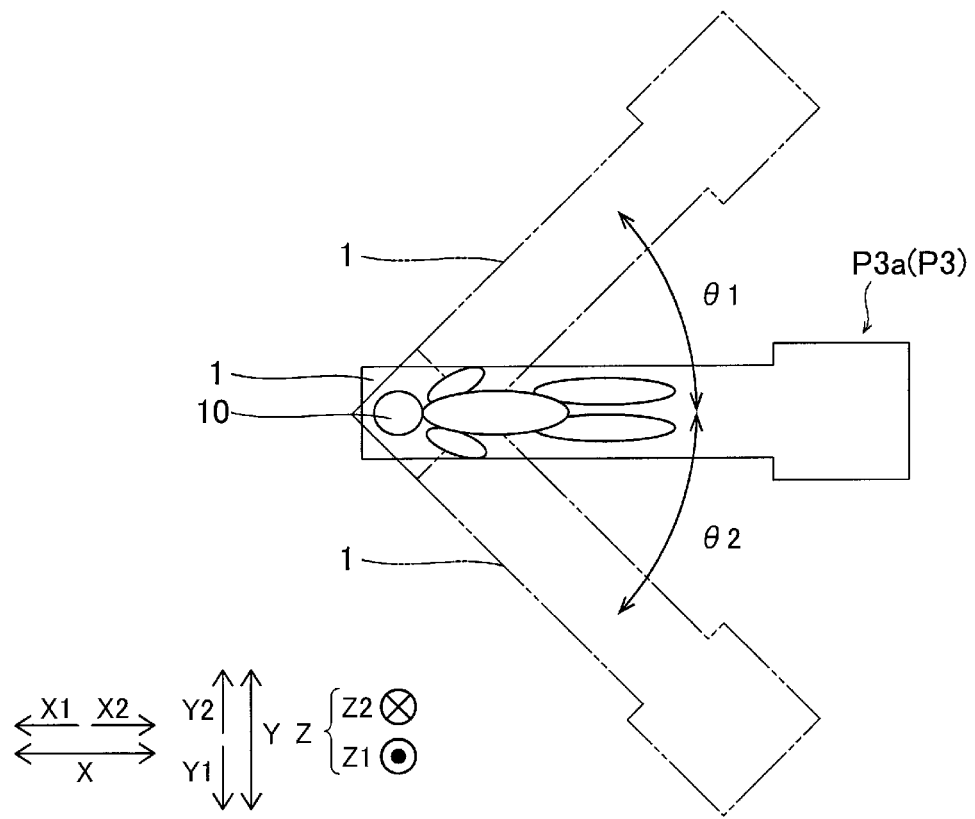
FIG. 8 is a view illustrating a rotation movement range of a robotic operating table according to one or more embodiments about the head side of a patient.

Moreover, in one or more embodiments, as illustrated in FIG. 8, the robotic arm 2 is configured to arrange the table 1 at the surgical operation position P4 at which the table 1 is rotated, from the state where the table 1 is horizontally arranged at the imaging position P3a, about a position adjacent to the other end of the table 1 in the longitudinal direction (X direction) thereof (head side of the patient 10 placed on the table 1) in a horizontal plane within a range of 10 degrees or more and 45 degrees or less. The surgical operation can be thus performed with the table 1 arranged at the surgical operation position P4 at which the table 1 is rotated, from the state where the table 1 is horizontally arranged at the imaging position P3a, about the position adjacent to the other end of the table 1 in the longitudinal direction thereof (head side of the patient 10 placed on the table 1) in the horizontal plane within the rotation range of 10 degrees or more and 45 degrees or less. Freedom in the adjustment of the surgical operation position P4 can be thereby increased. As a result, at the surgical operation position P4, it is possible to provide a space where the surgeon M1 stands on the head side of the patient 10 and a space where the other medical staffs M2 stand beside the operating table (table 1). Moreover, the robotic arm 2 is configured to be capable of rotating the table 1, from the state where the table 1 is horizontally arranged at the imaging position P3a, toward the left side of the patient about the position adjacent to the other end of the table 1 in the longitudinal direction thereof (head side of the patient 10) within a range θ1 which is 0 degrees or more and 45 degrees or less. Furthermore, the robotic arm 2 is configured to be capable of rotating the table 1, from the state where the table 1 is horizontally arranged at the imaging position P3a, toward the right side of the patient about the position adjacent to the other end of the table 1 in the longitudinal direction thereof (head side of the patient 10) within a range θ2 that is 0 degrees or more and 45 degrees or less.

In FIGS. 6A to 6E, the candidate positions P4a to P4e are illustrated as examples of the surgical operation position P4. Note that, in FIGS. 6A to 6E, the table 1 at the imaging position P3a is illustrated by two-dot chain lines to facilitate the understanding. As illustrated in FIG. 6A, the candidate position P4a may be a position where the table 1 is translated from the imaging position P3a in the Y1 direction (see FIG. 7) which is the direction toward the right side of the patient 10 by 400 mm. As illustrated in FIG. 6B, the candidate position P4b may be a position where the table 1 is translated from the imaging position P3a by 200 mm in the X2 direction (see FIG. 7) which is the direction toward the foot side of the patient 10 and by 340 mm in the Y1 direction which is the direction toward the right side of the patient 10. As illustrated in FIG. 6C, the candidate position P4c may be a position where the table 1 is translated from the imaging position P3a in the X2 direction which is the direction toward the foot side of the patient 10 by 400 mm. As illustrated in FIG. 6D, the candidate position P4d may be a position where the table 1 is rotated 15 degrees from the state where the table 1 is horizontally arranged at the imaging position P3a toward the left side of the patient 10 about the position adjacent to the other end of the table 1 in the longitudinal direction thereof (head side of the patient 10 placed on the table 1). As illustrated in FIG. 6E, the candidate position P4e may be a position where the table 1 is rotated 25 degrees from the state where the table 1 horizontally arranged at the imaging position P3a toward the left side of the patient 10 about the position adjacent to the other end of the table 1 in the longitudinal direction thereof (head side of the patient 10 placed on the table 1). Moreover, at the surgical operation position P4 (position selected from the candidate positions P4a to P4e), the table 1 may be disposed such that the one side of the table 1 in the longitudinal direction thereof being on the head side of the patient 10 faces the side where the radiographic imaging apparatus 300 is disposed and the other side of the table 1 in the longitudinal direction thereof being on the foot side of the patient 10 faces opposite to the side where the radiographic imaging apparatus 300 is disposed. When the surgical operation is performed at the surgical operation position P4, the ceiling-suspended radiographic imaging apparatus 300a, the floor-standing radiographic imaging apparatus 300b, the display 400, the anesthesia machine 502, the infusion device 503, the syringe pump 504, the surgical microscope device 505, a machine table 507, and the like may be disposed around the table 1. Moreover, at the surgical operation position P4, the surgeon M1 and the other medical staffs M2 may stand around the table 1.

As illustrated in FIGS. 6A to 6E, the robotic arm 2 is configured to take a posture not protruding from the leading side of the table 1 in the movement, in the state where the table 1 is disposed at the surgical operation position P4 (position selected from the candidate positions P4a to P4e). Moreover, the robotic arm 2 is configured to take such a posture that a portion of the robotic arm 2 protruding from the opposite side to the leading side of the table 1 in the movement protrudes from the first longitudinal half of the table in the X2 direction, in the state where the table 1 is disposed at the surgical operation position P4 (position selected from the candidate positions P4a to P4e).

Figure 9:
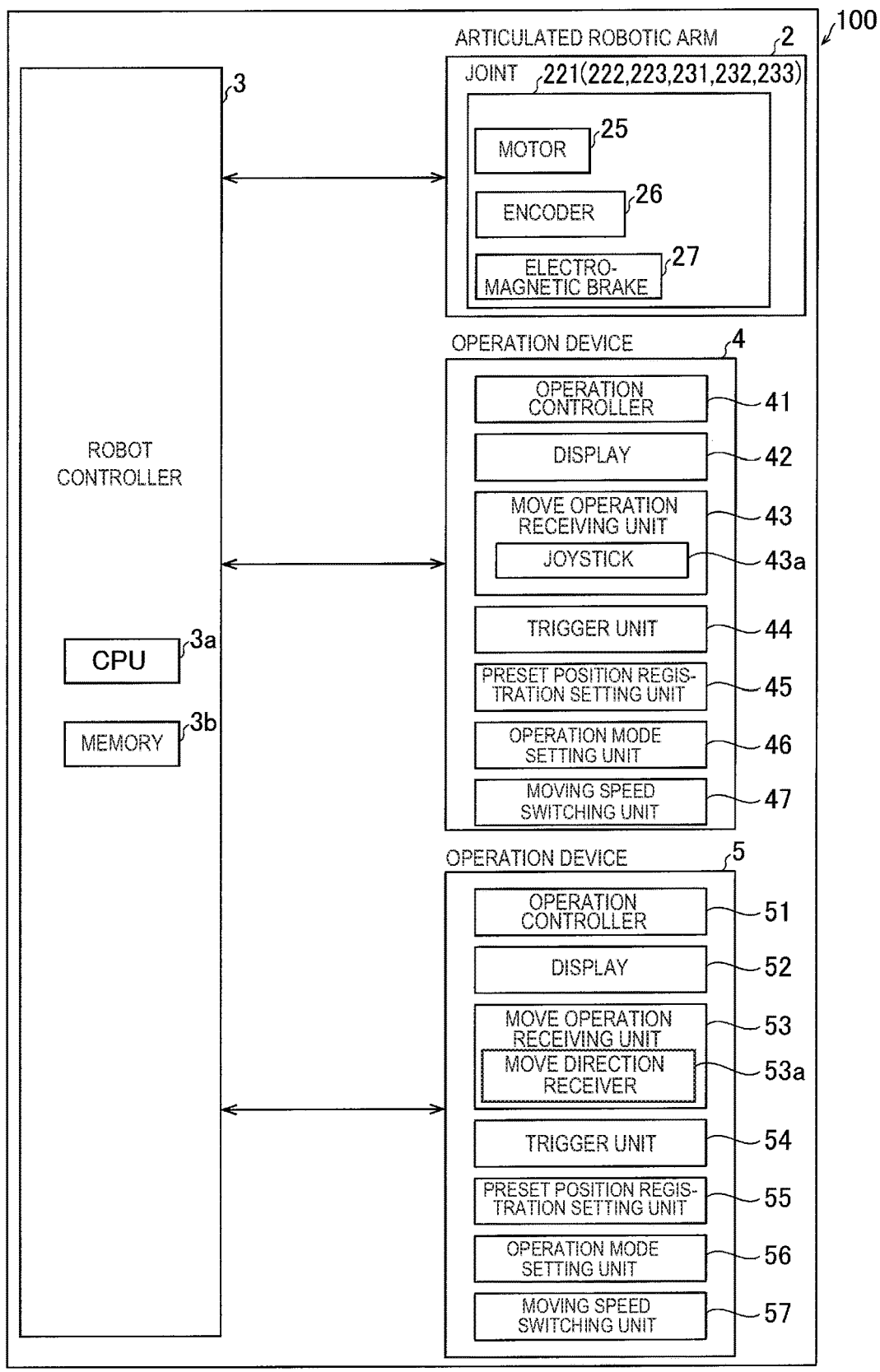
FIG. 9 is a block diagram illustrating a control configuration of a robotic operating table according to one or more embodiments.

As illustrated in FIG. 9, the joints (horizontal joints 221 to 223 and vertical joints 231 to 233) of the robotic arm 2 each include a motor 25, an encoder 26, an electromagnetic brake 27, and a decelerator (not illustrated). The motor 25 is a drive source for rotating the table 1 with the joint. The motor 25 includes a servo motor. Moreover, the motor 25 is configured to be driven by being controlled by the robot controller 3. The encoder 26 is configured to measure a rotation amount of the motor 25. Moreover, the encoder 26 is configured to send a measurement result of the rotation amount of the motor 25 to the robot controller 3. The robot controller 3 is configured to acquire position information of the table 1, posture information of the table 1, and posture information of the robotic arm 2 based on the measurement result of the encoder 26. The electromagnetic brake 27 may be used to brake the rotation of the motor 25 and actuated when not excited. Specifically, the electromagnetic brake 27 is configured to cancel the braking of the motor 25 when the power to the motor 25 is turned on and brake the motor 25 when the power to the motor 25 is turned off. The electromagnetic brake 27 may be an electromagnetic brake incorporated in the motor 25 or an electromagnetic brake provided externally to the motor 25.

The robot controller 3 is a control circuit including, for example, a CPU (Central Processing Unit) 3a and a memory 3b. The memory 3b according to one or more embodiments may include such devices as a flash memory device, magnetic disk device such as a hard disk drive, and an optical disk device that reads data from a recording medium. In one or more embodiments, for example, the recording medium may include Blu-ray disk, CD-ROM (Compact Disk Read Only Memory), DVD (Digital Versatile Disk). The robot controller 3 is disposed in the base 21 and is configured to control the movement of the table 1 by the robotic arm 2. Specifically, the robot controller 3 is configured to move the table 1 by controlling the movement of the robotic arm 2 based on operations performed by the medical staff (user).

Figure 10:
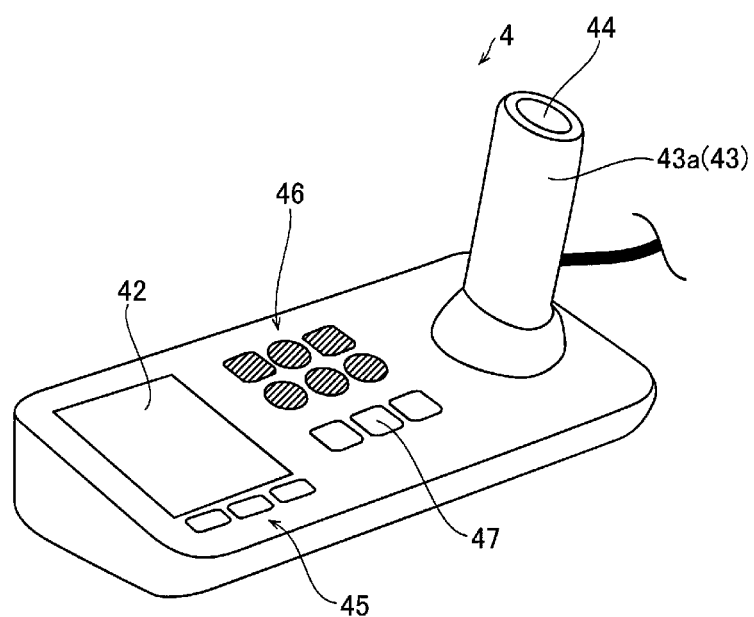
FIG. 10 is a perspective view illustrating an operation device of a robotic operating table according to one or more embodiments that includes a joystick.
Figure 11:
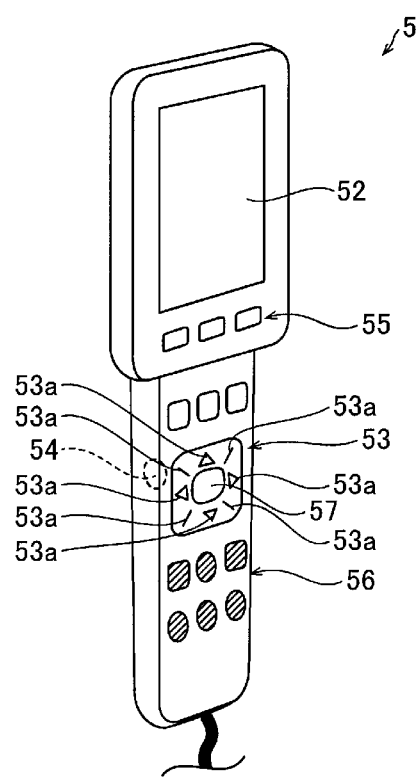
FIG. 11 is a perspective view illustrating an operation device of a robotic operation table according to one or more embodiments that includes move direction receivers.

As illustrated in FIGS. 9 to 11, the operation device 4 and the operation device 5 are configured to receive operations for moving the table 1 performed by the medical staff (user). The operation devices 4 and 5 can each receive the operations for the table 1. The operation device 4 is mainly used while being attached to the table 1. The operation device 5 is mainly used at a position away from the table 1. The operation devices 4 and 5 are configured to be detachably attached to the table 1 by engaging with engagement portions (not illustrated) provided on a side surface of the support unit 12 of the table 1. The operation devices 4 and 5 are connected to the robot controller 3 in such a way as to perform wired communication.

As illustrated in FIGS. 9 and 10, the operation device 4 includes an operation controller 41, a display 42, a move operation receiving unit 43, a trigger unit 44, a preset position registration setting unit 45, an operation mode setting unit 46, and a moving speed switching unit 47. As illustrated in FIGS. 9 and 11, the operation device 5 includes an operation controller 51, a display 52, a move operation receiving unit 53, a trigger unit 54, a preset position registration setting unit 55, an operation mode setting unit 56, and a moving speed switching unit 57.

The operation controller 41 (51) is configured to control the units in the operation device 4 (5) based on the operations performed by the medical staff (user). For example, the operation controller 41 (51) is configured to control images displayed on the display 42 (52) based on the operations performed by the medical staff (user). Moreover, the operation controller 41 (51) is configured to send operation information indicating the operations performed by the medical staff (user) to the robot controller 3. The robot controller 3 is configured to perform control of moving the table 1 with the robotic arm 2 based on the received operation information.

The display 42 (52) is configured to display the state of the table 1, the state of the operations performed on the operation device 4 (5), the operation screen, and the like. The display 42 (52) includes a liquid crystal display or an organic EL (Electro Luminescence) display. Moreover, in the operating room 200, the robot controller 3 and the operation controller 41 (51) of the robotic operating table 100 are communicably connected to the display 400 (see FIG. 1). The display 400 is configured to be capable of displaying the state of the table 1, the state of operations performed on the operation device 4 (5), the operation screen, and the like. For example, the display 400 is configured to be capable of displaying the image displayed on the display 42 (52) of the operation device 4 (5). In the operating room 200, the multiple medical staffs can thus check the operation state of the robotic operating table 100 at once. Moreover, the display 400 may be a touch panel type input and display and be configured to receive the operation for moving the table 1 from the medical staff (user) operating the screen.

The move operation receiving unit 43 (53) is configured to receive a move operation of the table 1 given by the medical staff (user). In the operation device 4, the move operation receiving unit 43 includes a joystick 43a. The joystick 43a is configured to be operated by being tilted. Moreover, the joystick 43a is configured to receive the operation of moving the table 1 depending on the direction and angle of tilt. In the operation device 5, the move operation receiving unit 53 includes multiple (eight) move direction receivers 53a provided respectively for the directions in which the table 1 is to be moved. In other words, the move direction receivers 53a are provided for eight directions. Moreover, the move direction receivers 53a are configured to receive the operation of moving the table 1 by being pressed. Note that the eight move direction receivers 53a are configured to be lighted by light sources being light-emitting diodes provided in the move direction receivers 53a.

The trigger unit 44 (54) is provided to enable the operation on the move operation receiving unit 43 (53). Specifically, the trigger unit 44 (54) has a function of turning on the power to the motors 25 by being operated. The robot controller 3 is configured to perform control of supplying the power to the motors 25 while the trigger unit 44 is being operated. Operating the trigger unit 44 (54) thus cancels the braking of the motors 25 by the electromagnetic brakes 27. As a result, the operation on the move operation receiving unit 43 (53) is enabled while the trigger unit 44 (54) is being operated, and the table 1 can be moved. Moreover, in the robotic operating table 100, the power to the motors 25 is turned off when the operation of the trigger unit 44 (54) is canceled. The robot controller 3 is configured to stop energization of the motors 25 and actuate the electromagnetic brakes 27 when the trigger unit 44 (54) is not operated. Cancelling the operation on the trigger unit 44 (54) can thus cause the electromagnetic brakes 27 to brake the motors 25. As a result, when the trigger unit 44 (54) is not operated, the operation on the move operation receiving unit 43 (53) is disabled and the table 1 cannot be moved. Since the table 1 is not moved unless the trigger unit 44 (54) is operated, it is possible to prevent the table 1 from being unintentionally moved when the move operation receiving unit 43 (53) is unintentionally operated.

In the operation device 4, the trigger unit 44 may be provided at a distal end of the joystick 43a. In the operation device 4, pressing the trigger unit 44 enables the operation on the joystick 43a. Moreover, the operation on the joystick 43a is disabled in the state where the pressing of the trigger unit 44 is canceled. In the operation device 5, the trigger unit 54 may be provided on a surface opposite to a surface on which the move direction receivers 53a are provided. In the operation device 5, pressing the trigger unit 54 enables the operation on the move direction receivers 53a. Moreover, the operation on the move direction receivers 53a is disabled in the state where the pressing of the trigger unit 54 is canceled.

In one or more embodiments, the robot controller 3 is configured to control the movement of the robotic arm 2 such that the robotic arm 2 moves the table 1 while the move operation receiving unit 43 (53) is receiving the move operation. Specifically, in one or more embodiments, for example, when the table 1 is moved from the imaging position P3a (see FIGS. 5A to 5D) to the surgical operation position P4, the table 1 is moved toward the surgical operation position P4 only while the move operation receiving unit 43 (53) is receiving the move operation. The table 1 is thus not moved unless the move operation receiving unit 43 (53) receives the move operation. Accordingly, when the move operation receiving unit 43 (53) is unintentionally operated, the table 1 can be prevented from being unintentionally continuously moved. Moreover, when the table 1 is intentionally moved, the movement of the table 1 can be stopped only by stopping the operation on the move operation receiving unit 43 (53). As a result, when the movement of the table 1 is desired to be stopped in the middle of the movement of the table 1, the movement of the table 1 can be easily and quickly stopped.

Specifically, the robot controller 3 is configured to control the movement of the robotic arm 2 such that, when the operation device 4 receives the operation performed by the medical staff (user), the robotic arm 2 moves the table 1 while the joystick 43a is being operated. In other words, when the operation device 4 receives the operation performed by the medical staff (user), the table 1 is moved only while the joystick 43a is being operated.

Moreover, the robot controller 3 is configured to control the movement of the robotic arm 2 such that, when the operation device 5 receives the operation performed by the medical staff (user), the robotic arm 2 moves the table 1 while one of the move direction receivers 53a is being operated. In other words, when the operation device 5 receives the operation performed by the medical staff (user), the table 1 is moved only while the move direction receivers 53a are being operated.

Moreover, the robot controller 3 is configured to control the movement of the robotic arm 2 such that, when one of the operation devices 4 and 5 receives the operation performed by the medical staff (user), the robotic arm 2 moves the table 1 while the trigger unit 44 (54) and the move operation receiving unit 43 (53) are being simultaneously operated. In other words, when the operation device 4 receives the operation performed by the medical staff (user), the table 1 is moved only while the operation of pressing the trigger unit 44 and the operation of tilting the joystick 43a are being simultaneously performed. Moreover, when the operation device 5 receives the operation performed by the medical staff (user), the table 1 is moved only while the operation of pressing the trigger unit 54 and the operation of pressing one of the move direction receivers 53a are being simultaneously performed. The table 1 is thus not moved unless the trigger unit 44 (54) and the move operation receiving unit 43 (53) are both operated. Accordingly, when the move operation receiving unit 43 (53) is unintentionally operated, the table 1 can be prevented from being unintentionally moved.

The preset position registration setting unit 45 (55) is provided to set a movement destination of the table 1 as a preset position and to register the current position of the table 1 as the preset position. In one or more embodiments, by registering the preset position in advance, the table 1 can be easily disposed at the preset position registered in advance. The preset position registration setting unit 45 (55) is configured to receive an operation of setting the movement destination of the table 1 as the preset position and an operation of registering the current position of the table 1 as the preset position by being pressed. When the current position of the table 1 is registered as the preset position by using the preset position registration setting unit 45 (55), information on the registered preset position is stored in the memory 3b of the robot controller 3. Specifically, the position information of the table 1 and the posture information of the robotic arm 2 at this time are stored in the memory 3b of the robot controller 3. Moreover, the preset position registration setting unit 45 (55) is configured such that giving a registration operation on the preset position registration setting unit 45 (55) with the table 1 disposed at a certain position causes a certain position (current position) to be stored in the memory 3b as the preset position. By operating the trigger unit 44 (54) and the move operation receiving unit 43 (53) in a state where the preset position is selected by using the preset position registration setting unit 45 (55), the table 1 is moved to the selected preset position. In one or more embodiments, the preset position includes the anesthetization position P2, the imaging position P3, and the surgical operation position P4. The table 1 can be thereby easily disposed at any of the anesthetization position P2, the imaging position P3, and the surgical operation position P4 desired by the medical staff.

The operation mode setting unit 46 (56) is provided to set an operation mode to one of the preset multiple operation modes. The operation mode setting unit 46 (56) is configured to receive a setting operation for the operation mode given by the user. The multiple operation modes include, for example, a plane rotation mode of rotating the table 1 in a horizontal plane about a rotation axis extending in the vertical direction (Z direction), a plane movement mode of linearly moving the table 1 in a horizontal plane, a lifting-lowering mode of moving table 1 up and down, a roll mode of rotating the table 1 about an axis extending parallel to the longitudinal direction (X direction) of the table 1, and a pitch mode of rotating the table 1 about an axis extending parallel to the transverse direction (Y direction) of the table 1. In the plane rotation mode, the table 1 is caused to yaw based on the operation performed by the medical staff (user). In the plane movement mode, the table 1 is linearly moved in the horizontal direction based on the operation performed by the medical staff (user). In the lifting-lowering mode, the table 1 is moved in the vertical direction (Z direction) based on the operation performed by the medical staff (user). In the roll mode, the table 1 is caused to roll based on the operation performed by the medical staff (user). In the pitch mode, the table 1 is caused to pitch based on the operation performed by the medical staff (user). The user sets one of the multiple operation modes depending on a desired operation by using the operation mode setting unit 46 (56). In the robotic operating table 100, the table 1 is moved by operating the trigger unit 44 (54) and the move operation receiving unit 43 (53) in a state where the operation mode is selected by using the operation mode setting unit 46 (56).

The moving speed switching unit 47 (57) is configured to receive an operation of changing the moving speed of the table 1 given by the user. Moreover, the moving speed switching unit 47 (57) is configured to receive an operation of changing the moving speed of the table 1 by being pressed. The robotic operating table 100 is configured to change the moving speed of the table 1 stepwise every time the moving speed switching unit 47 (57) is pressed. For example, the moving speed of the table 1 can be switched among three stages of moving speed.

(Configuration of Radiographic Imaging Apparatus)

A configuration of the radiographic imaging apparatus 300 is described with reference to FIG. 1.

As illustrated in FIG. 1, the radiographic imaging apparatus 300 is configured to be capable of capturing a radiographic projection image of the patient 10 placed on the table 1 of the robotic operating table 100. The radiographic imaging apparatus 300 includes an X-ray irradiation unit 301, an X-ray detection unit 302, and a C-arm 303. The X-ray irradiation unit 301 and the X-ray detection unit 302 are supported by the C-arm 303. The X-ray irradiation unit 301 and the X-ray detection unit 302 are moved with movement of the C-arm 303 and are disposed to face each other with the patient 10 therebetween when the patient 10 is imaged by using X-ray. For example, one of the X-ray irradiation unit 301 and the X-ray detection unit 302 is disposed in a space above the table 1 and the other is disposed in a space below the table 1. Moreover, when the patient 10 is imaged by using X-ray, portions of the C-arm 303 supporting the X-ray irradiation unit 301 and the X-ray detection unit 302 are disposed in the spaces above and below the table 1.

The X-ray irradiation unit 301 is disposed to face the X-ray detection unit 302. Moreover, the X-ray irradiation unit 301 is configured to be capable of emitting X-ray toward the X-ray detection unit 302. The X-ray detection unit 302 is configured to detect the X-ray emitted from the X-ray irradiation unit 301. The X-ray detection unit 302 includes a FPD (Flat Panel Detector). The X-ray detection unit 302 is configured to convert the detected X-ray into an electric signal and send the electric signal to an image processor (not illustrated).

The X-ray irradiation unit 301 is connected to one end of the C-arm 303, and the X-ray detection unit 302 is connected to the other end of the C-arm 303. The C-arm 303 has a substantially C shape. In the imaging of the patient 10 using X-ray, the C-arm 303 can thereby support the X-ray irradiation unit 301 and the X-ray detection unit 302 so that the table 1 and the patient 10 are located between the X-ray irradiation unit 301 and the X-ray detection unit 302. The C-arm 303 is configured to be movable relative to the table 1. Specifically, the C-arm 303 is configured to be movable in the horizontal direction and the vertical direction and to be rotatable about a rotation axis extending in the horizontal direction and a rotation axis extending in the vertical direction. The X-ray irradiation unit 301 and the X-ray detection unit 302 can be thereby disposed at desired positions relative to the patient 10 placed on the table 1. The C-arm 303 is configured to be moved by a drive unit (not illustrated) based on an operation performed by the medical staff (user). Moreover, the C-arm 303 is configured to be manually movable by the medical staff (user). Furthermore, the radiographic imaging apparatus 300 and the display 400 are communicably connected to each other, and the display 400 is configured to be capable of displaying the radiographic fluoroscopic image captured by the radiographic imaging apparatus 300 and the radiographic image captured by the radiographic imaging apparatus 300.

MODIFIED EXAMPLES

Note that one or more embodiments disclosed herein should be considered as exemplary in all respects and does not limit the present invention. The scope of the present invention is defined not by the description of the aforementioned one or more embodiments but by the scope of claims, and includes all equivalents and all modifications (modified examples) within the scope of claims.

For example, although the example in which the radiographic imaging apparatus is provided in the hybrid operating room is described in the aforementioned one or more embodiments, the present invention is not limited to this. In one or more embodiments, a magnetic resonance imaging apparatus for capturing a magnetic resonance image of the patient may be provided in the hybrid operating room. In other words, the operating room system may include the robotic operating table and the magnetic resonance imaging apparatus. Moreover, both of the radiographic imaging apparatus and the magnetic resonance imaging apparatus may be provided in the hybrid operating room. In other words, the operating room system may include the robotic operating table, the radiographic imaging apparatus, and the magnetic resonance imaging apparatus.

Figure 12:
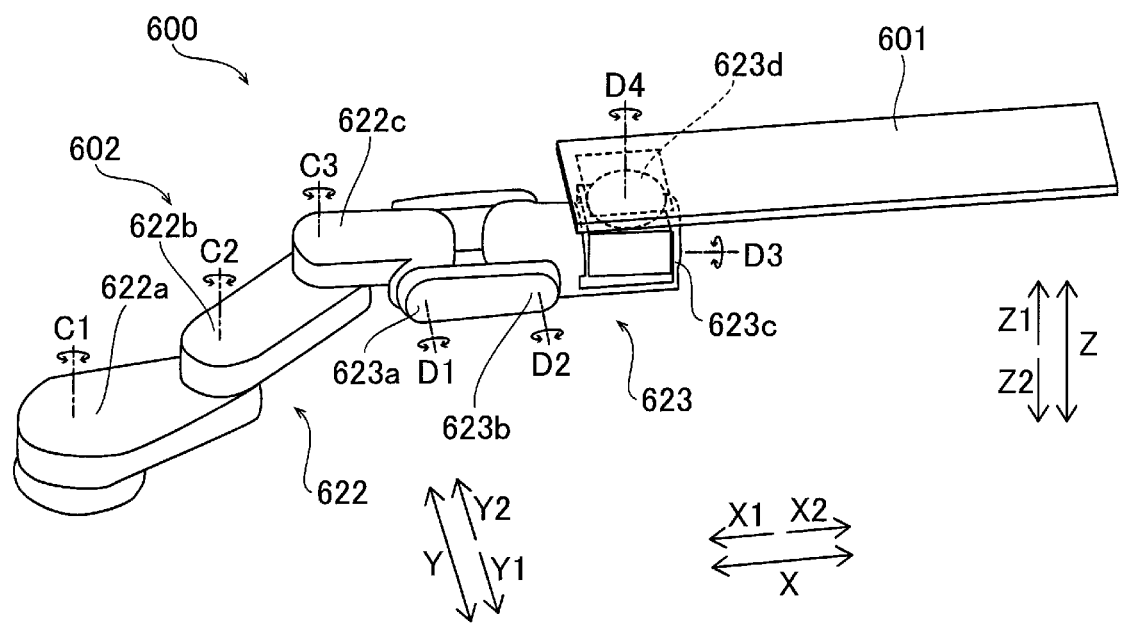
FIG. 12 is a perspective view illustrating a robotic operating table according to a modified example of one or more embodiments.

Although the example in which the articulated robotic arm is configured such that the Y direction translatable range of the table, from the imaging position or from the position translated from the imaging position in the X direction, in the direction toward the one side of the Y direction is different from that in the direction toward the other side of the Y direction is described in the aforementioned one or more embodiments, the present invention is not limited to this. In one or more embodiments, the articulated robotic arm may be configured such that the Y direction translatable range of the table, from the imaging position or from the position translated from the imaging position in the X direction, in the direction toward the one side of the Y direction is the same as that in the direction toward the other side of the Y direction. For example, in the modified example illustrated in FIG. 12, a robotic operating table 600 includes a table 601 on which a patient is placed and an articulated robotic arm 602. The articulated robotic arm 602 includes a horizontal articulated assembly 622 and a vertical articulated assembly 623. The horizontal articulated assembly 622 includes horizontal joints 622a, 622b, and 622c. The vertical articulated assembly 623 includes vertical joints 623a and 623b, a roll rotation joint 623c, and a yaw rotation joint 623d. Note that the horizontal joints 622a, 622b, 622c, the vertical joints 623a, 623b, the roll rotation joint 623c, and the yaw rotation joint 623d are examples of "joints" in one or more recited embodiments. The articulated robotic arm 602 is configured to move the table 1 with seven degrees of freedom. Specifically, the articulated robotic arm 602 has three degrees of freedom of rotation about a rotation axis C1, rotation about a rotation axis C2, and rotation about a rotation axis C3 that are provided by the horizontal articulated assembly 622. Moreover, the articulated robotic arm 602 has four degrees of freedom of rotating about a rotation axis D1, rotating about a rotation axis D2, rotating about a rotation axis D3, and rotating about a rotation axis D4 that are provided by the vertical articulated assembly 623. The articulated robotic arm in the modified example is configured such that the Y direction translatable range of the table 601, from the imaging position or from the position translated from the imaging position in the X direction, in the direction toward the one side of the Y direction is the same as that in the direction toward the other side of the Y direction. Moreover, the articulated robotic arm 602 in the modified example is configured to be capable of translating the table 601, from the imaging position P3a or from the position translated from the imaging position P3a in the X direction, within a range of 800 mm or less in the direction (Y1 direction) toward the one side of the Y direction and also within a range of 800 mm or less in the direction (Y2 direction) toward the other side of the Y direction, and can thus translate the table 601 within a range of 1600 mm or less in total. Furthermore, the articulated robotic arm 602 in the modified example is configured to be capable of translating the table 601, from the state where the table 601 is horizontally arranged at the imaging position P3a, within a range of 1000 mm or less in the direction (X1 direction) toward the one side of the X direction and also within a range of 1000 mm or less in the direction (X2 direction) toward the other side of the X direction, and can thus translate the table 601 within a total range of 2000 mm or less.

Moreover, although the example in which the articulated robotic arm is configured such that the Y direction translatable range of the table, from the imaging position or from the position translated from the imaging position in the X direction, in the Y2 direction is greater than that in the Y1 direction is described in the aforementioned one or more embodiments, the present invention is not limited to this. In one or more embodiments, the articulated robotic arm may be configured such that the Y direction translatable range of the table, from the imaging position or from the position translated from the imaging position in the X direction, in the Y1 direction is greater than that in the Y2 direction.

Furthermore, although the example in which the two operation devices are provided in the robotic operating table is described in the aforementioned one or more embodiments, the present invention is not limited to this. In one or more embodiments, one operation device or three or more operation devices may be provided in the robotic operating table.

Moreover, although the example in which the operation devices are connected to the robot controller in such a way as to perform wired communication is described in the aforementioned one or more embodiments, the present invention is not limited to this. For example, the operation devices may be connected to the robot controller in such a way as to perform wireless communication.

Furthermore, although the example in which the horizontal articulated assembly includes three horizontal joints is described in the aforementioned one or more embodiments, the present invention is not limited to this. In one or more embodiments, the horizontal articulated assembly may include two horizontal joints or four or more horizontal joints.

Moreover, although the example in which the vertical articulated assembly includes three vertical joints is described in the aforementioned one or more embodiments, the present invention is not limited to this. In one or more embodiments, the vertical articulated assembly may include two vertical joints or four or more vertical joints.

Furthermore, although the example in which the articulated robotic arm is provided with three horizontal joints in series and with three vertical joints in series is described in the aforementioned one or more embodiments, the present invention is not limited to this. In one or more embodiments, for example, a vertical articulated robot including multiple portions in which rotating axes of adjacent joints are orthogonal to each other may be used as the articulated robotic arm.

Moreover, although the example in which the articulated robotic arm has seven degrees of freedom is described in the aforementioned one or more embodiments, the present invention is not limited to this. In one or more embodiments, the articulated robotic arm may have six or less degrees of freedom or eight or more degrees of freedom. However, it is preferable that the articulated robotic arm has six or more degrees of freedom.

Furthermore, although the example in which the base is buried in and fixed to the floor is described in the aforementioned one or more embodiments, the present invention is not limited to this. In one or more embodiments, the base may be fixed onto the floor.

Moreover, although the example in which the robot controller is disposed in the base is described in the aforementioned one or more embodiments, the present invention is not limited to this. In one or more embodiments, the robot controller may be housed in a casing to form a control box and, for example, the control box may be disposed at an arbitrary location in the operating room. Alternatively, the control box may be disposed in a control center adjacent to the operating room.

The invention claimed is:

1. A patient placement table moving method for use with a robotic operating table comprising a patient placement table on which the patient is placed, a base that is buried in or fixed to a floor and an articulated robotic arm comprising a plurality of joints and having first and second ends, wherein the first end is supported on the base to be rotatable about an axis extending in a vertical direction, and the second end supports the patient placement table,
the method comprising:
horizontally arranging the patient placement table by the robotic arm at an imaging position for imaging with a medical imaging apparatus; and
translating the patient placement table from the imaging position to a surgical operation position by the robotic arm, wherein the surgical operation position is away from the imaging position by a distance of 200 mm or more in a second direction which is orthogonal to a first direction in a horizontal plane, and the first direction is parallel with a longitudinal direction of the patient placement table, wherein
the robotic operating table further comprises an operation device comprising a move operation receiving unit that receives a move operation of the patient placement table, and a trigger unit that enables an operation of the move operation receiving unit,
the robotic arm is configured to be disposed at the surgical operation position or the imaging position with the entire robotic arm hidden below the table, and
the method further comprises moving by the robotic arm, the patient placement table only while both the trigger unit and the move operation receiving unit are operated.

2. The method according to claim 1, wherein the surgical operation position is away from the imaging position by the distance of 200 mm or more and 800 mm or less in the second direction.

3. The method according to claim 1, wherein
the robotic arm is configured to translate the patient placement table in the second direction from the imaging position; and
a translatable range of the patient placement table in the second direction by the robot arm is 1200 mm or less.

4. The method according to claim 1, wherein
the robotic arm is configured to translate the patient placement table in the first direction or an opposite direction to the first direction from the imaging position; and a total translatable range of the patient placement table in the first direction and the opposite direction by the robot arm is 2000 mm or less.

5. The method according to claim 1, wherein
the imaging position and the surgical operation position are registered by the operation device, and
in a condition in which the surgical operation position or the imaging position is set as a movement destination of the patient placement table by the operation device, the move operation receiving unit receives the move operation and the trigger unit is operated, the robotic arm moves the patient placement table toward the surgical operation position or the imaging position.

6. The method according to claim 1, wherein
an anesthetization position is registered by the operation device, and
in a condition in which the anesthetization position is set as a movement destination of the patient placement table by the operation device, the move operation receiving unit receives the move operation and the trigger unit is operated, the robotic arm moves the patient placement table toward the anesthetization position.

7. The method according to claim 1, wherein
the robotic arm comprises joints,
each of the joints comprises a motor and an electromagnetic brake, and
the robotic arm stops energization of the motor and actuates the electromagnetic brake while the trigger unit is not operated, and
the robotic arm energizes the motor and does not actuate the electromagnetic brake while the trigger unit is operated.

8. The method according to claim 1, wherein the robotic arm moves the patient placement table with six or more degrees of freedom and causes the patient placement table at the imaging position to roll, pitch, and yaw.

9. The method according to claim 1, wherein the robotic arm comprises:
a horizontal articulated assembly comprising horizontal joints; and
a vertical articulated assembly comprising vertical joints.

10. The method according to claim 1, wherein
the patient placement table comprises:
a radiolucent part; and
a support unit supporting the radiolucent part, and
the second end of the robotic arm supports the support unit.

11. The method according to claim 1, further comprising moving the patient placement table from the imaging position or the surgical operation position to a transfer position for transferring the patient from the patient placement table to a stretcher.

12. The method according to claim 1, wherein the medical imaging apparatus is at least one of a radiographic imaging apparatus that captures a radiographic projection image of the patient and a magnetic resonance imaging apparatus that captures a magnetic resonance image of the patient.

13. The method according to claim 1, wherein the move operation receiving unit includes a joystick or multiple move direction receivers.

14. A patient placement table moving method used on a robotic operating table including a patient placement table on which the patient is placed, a base that is buried in or fixed to a floor and an articulated robotic arm comprising a plurality of joints, and having first and second ends, wherein the first end is supported on the base to be rotatable about an axis extending in a vertical direction and the second end supports the table, the method comprising:

horizontally arranging the table by the robotic arm at an imaging position for imaging with a medical imaging apparatus;

translating the table from the imaging position to a certain position by the robotic arm, wherein the certain position is away from the imaging position by a distance of 1000 mm or less in a first direction parallel with a longitudinal direction of the table; and translating the table from the certain position to a surgical operation position, wherein the surgical operation position is away from the certain position by a distance of 200 mm or more in a second direction orthogonal to the first direction in a horizontal plane.

15. The method according to claim 14, wherein the certain position is away from the imaging position by the distance of 200 mm or more and 800 mm or less in the second direction.

16. The method according to claim 14, further comprising moving the table from the imaging position or the surgical operation position to a transfer position for transferring the patient from the table to a stretcher.

17. A patient placement table moving method with use a robotic operating table including a patient placement table on which the patient is placed, a base that is buried in or fixed to a floor and an articulated robotic arm comprising a plurality of joints, and having first and second ends, wherein the first end is supported on the base to be rotatable about an axis extending in a vertical direction and the second end supports a portion of the table on a first end side in a longitudinal direction of the table, the method comprising:

horizontally arranging the table by the robotic arm at an imaging position for imaging with a medical imaging apparatus; and moving the table by the robotic arm from the imaging position to a surgical operation position by rotating the table in a horizontal plane within a range of 10 degrees or more and 45 degrees or less about a vertical axis, which is positioned on a second end side in the longitudinal direction of the table.

18. The method according to claim 17, wherein the imaging position is a position for imaging a head of the patient.

19. The method according to claim 17, further comprising moving the table from the imaging position or the surgical operation position to a transfer position for transferring the patient from the table to a stretcher.

* * * * *